United States Patent [19]

Vis

[11] 3,938,503
[45] Feb. 17, 1976

[54] ACHILLES REFLEX TEST SYSTEM

[75] Inventor: Vincent A. Vis, Brighton, Mich.

[73] Assignee: J. M. Richards Laboratories, Grosse Pointe, Mich.

[22] Filed: Sept. 3, 1974

[21] Appl. No.: 502,718

[52] U.S. Cl................. 128/2 N; 307/232; 328/110; 328/150
[51] Int. Cl.² ........................................... A61B 5/16
[58] Field of Search .. 128/2 N, 2 S, 2.06 R, 2.06 A, 128/2.06 F; 328/110, 150; 307/232

[56] References Cited
UNITED STATES PATENTS

| | | | |
|---|---|---|---|
| 3,322,115 | 5/1967 | Richards | 128/2 N |
| 3,475,062 | 10/1969 | Crittenden et al. | 307/232 |
| 3,716,799 | 2/1973 | Haass et al. | 328/150 |
| 3,734,082 | 5/1973 | Rawson | 128/2 N |

OTHER PUBLICATIONS

Molcho et al., "Electronic Measurement of Achilles Tendon Reflex" IEEE Trans on Bio-Med Eng., Vol. 17, No. 4, Oct. 1970, pp. 353–355.
Bourne, "Meausrement of Achilles Tendon Reflex," Med. & Biol. Eng., Vol. 10, No. 5, pp. 692–696, 1972.
Tuck, "Improved Measurement of Ach. Tendon Reflex," Med. & Biol. Eng., Mar. 1974, pp. 170–173.
Roy et al., "Simple Linear Pulse to Pulse Cardiotech.", Med. & Biol. Eng. pp. 370–373, May 1974.

Primary Examiner—Robert W. Michell
Assistant Examiner—Lee S. Cohen
Attorney, Agent, or Firm—Gaylord P. Haas, Jr.

[57] ABSTRACT

A system for measuring the duration of the Achilles tendon reflex after the tendon has been tapped by a percussion hammer, the system including an input transducer which converts the reflex extension of the ankle joint to an electric signal which is fed to the input of an amplifier, the output of the amplifier being fed to a peak holder and to a comparator circuit. A portion of the signal from the peak holder is also fed to the comparator circuit which detects a crossover point of the two signals fed to the comparator. The first such crossover occurs during the hammer tap "artefact" and the second such crossover occurs during the relaxation phase of the reflex action. A timing device (such as an integrator) measures the time elapsed between the two crossovers and displays the result. The system also includes a reset switch which is interconnected with the peak holder, the flip flop, and the integrator circuits to reset those circuits and the system further includes an input offset compensator circuit, the output of the input offset compensator circuit being fed to the input circuit of the amplifier to provide sufficient current to reduce or increase the output of the amplifier to zero with zero input signal being fed to the input of the transducer.

24 Claims, 4 Drawing Figures

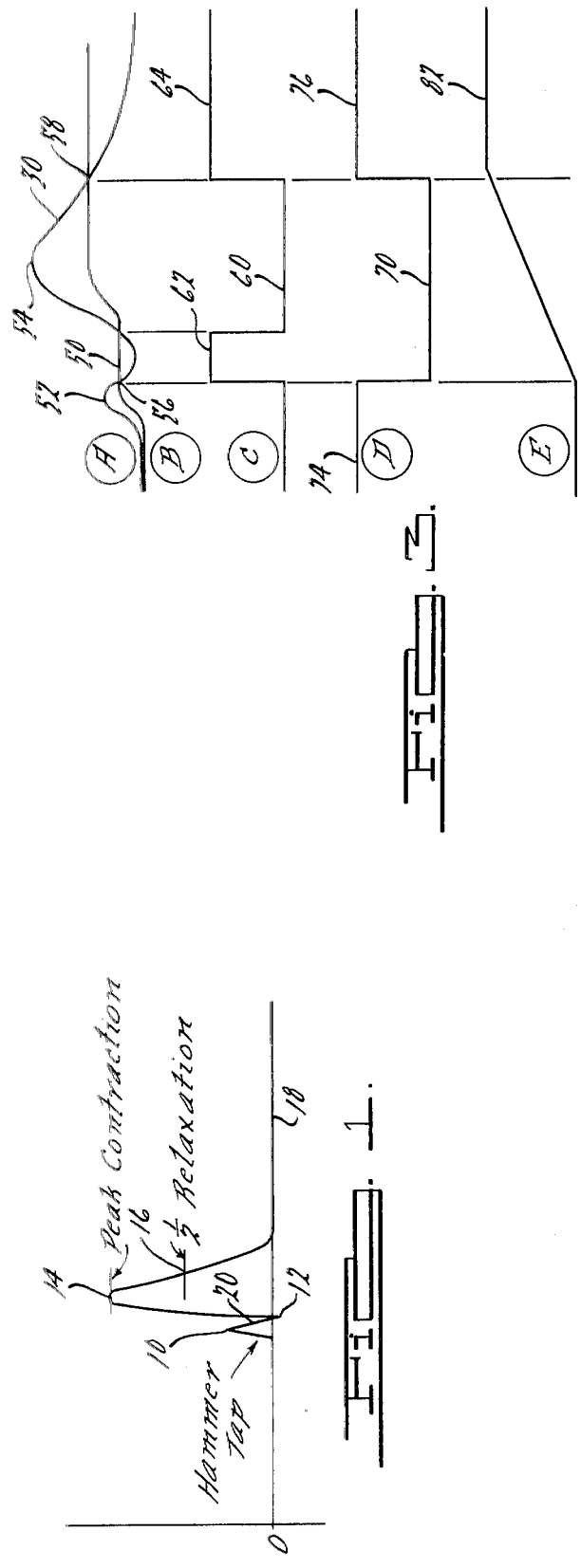
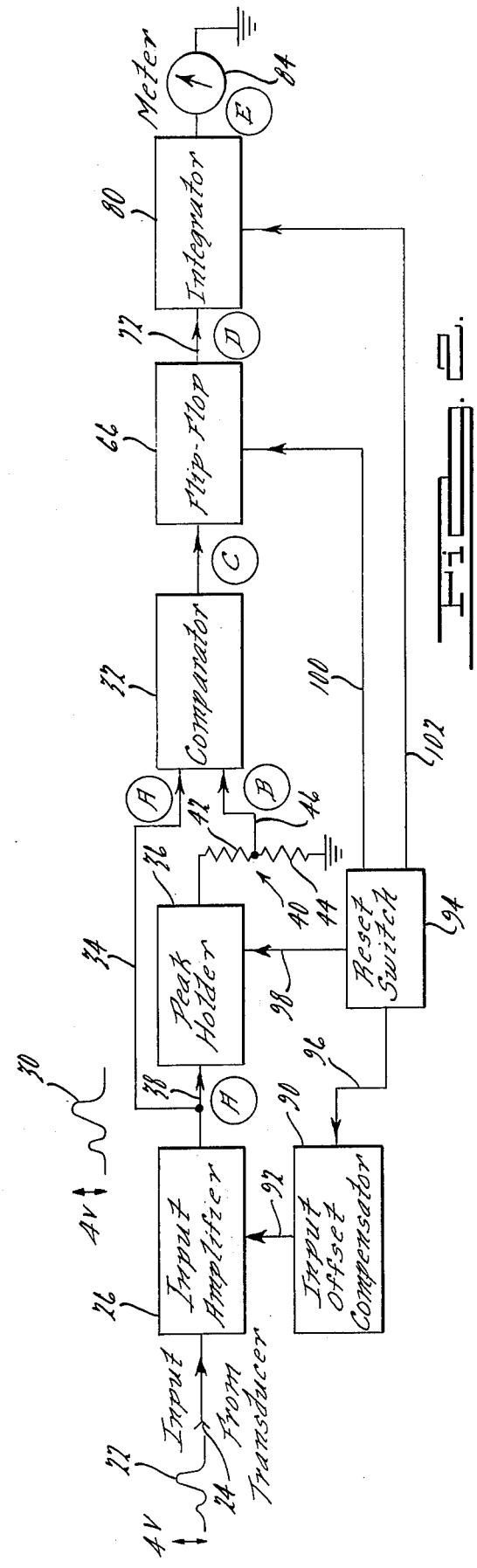

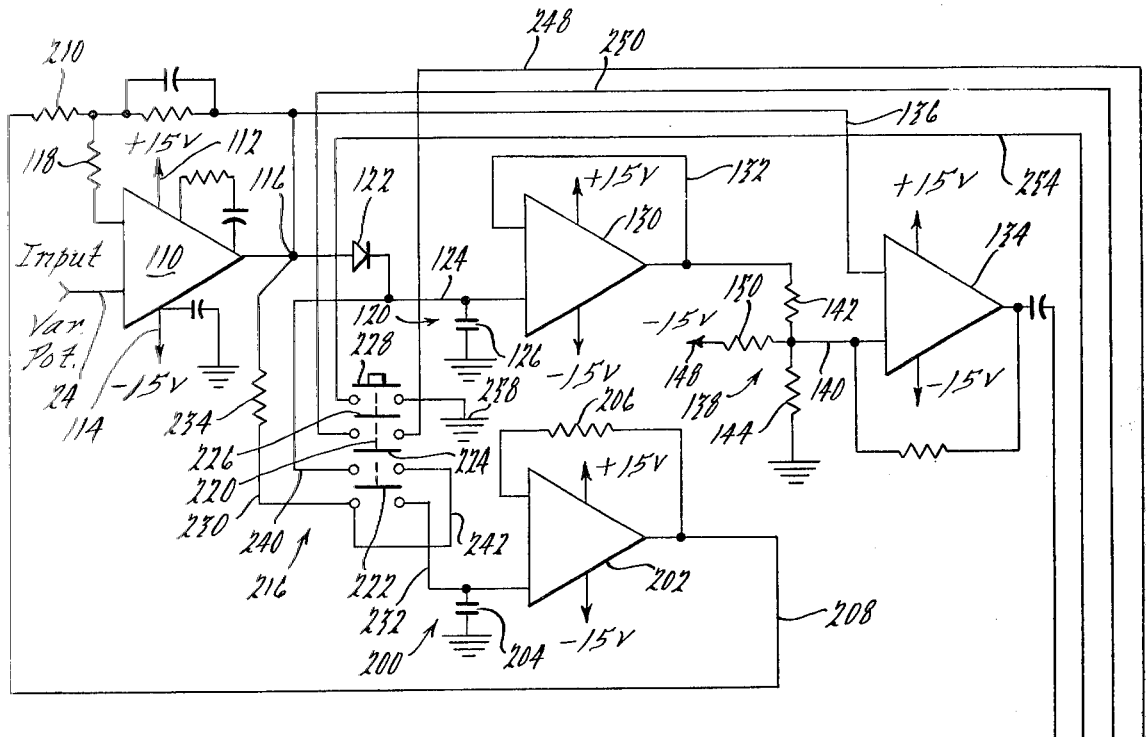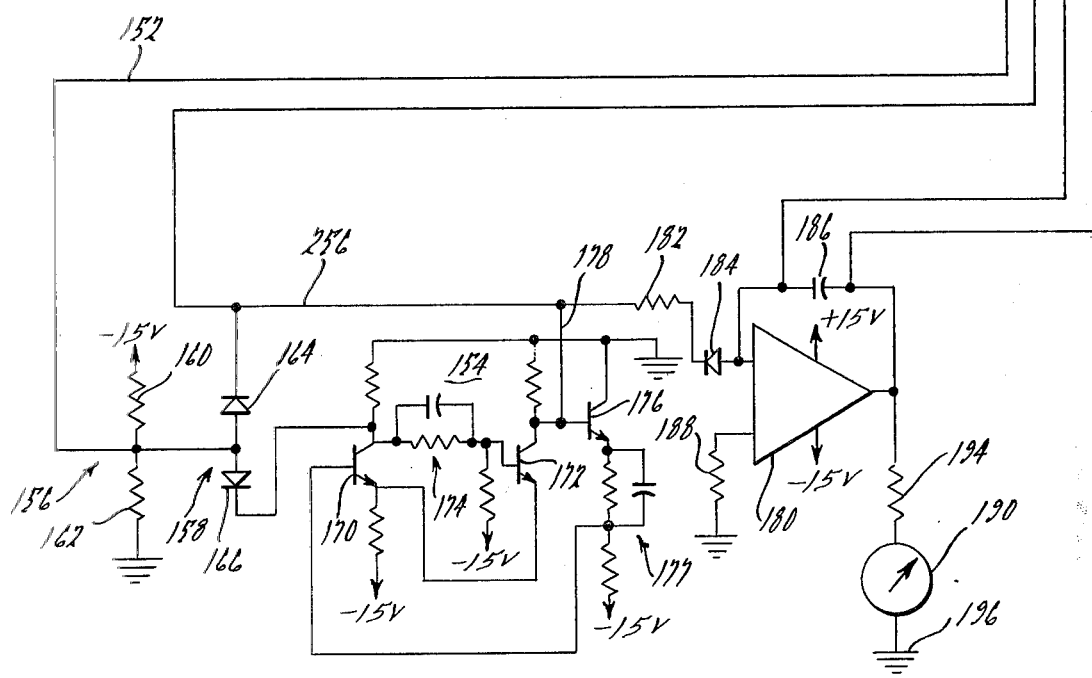
FIG. 4.

ACHILLES REFLEX TEST SYSTEM

BACKGROUND AND SUMMARY OF THE DISCLOSURE

This invention relates generally to an electrical apparatus adapted for use as a diagnostic aid in determining certain physical conditions of a patient, and more particularly, the present invention relates to an electrical apparatus which is designed to measure the reflex action of the Achilles tendon as an aid in the diagnosis of thyroid malfunctions and the treatment of those malfunctions.

The original concept for measuring the reflex duration of the Achilles tendon after it has been tapped by a reflex hammer consisted of a platform on which the patient's foot rested. Measurements of the reflex duration were made by observing the pressure changes on the platform under the foot. This pressure change could then be translated into a chart to form a permanent record for subsequent study and comparison. Certain subsequent systems utilized an apparatus which simplified the measuring of the reflex action and particularly utilized a strain-gauge transducer and an electro-optical system.

The concept of utilizing the reflex action of the Achilles tendon as an aid in the diagnosis of thyroid malfunctions and the like has been known in the past.

Certain prior art systems, for example, utilized a permanent magnet which is attached to the heel of the patient by use of adhesive tape. A measuring head, having a fixed electrical coil, is positioned a few inches from the magnet on the heel. The electrical coil in then connected to a standard ECG unit so as to produce a visual trace on a standard ECG chart. Thus, when the Achilles tendon is tapped with a reflex hammer, the movement of the magnet with respect to the coil will produce an impulse whose shape will determine the visual trace on the ECG chart.

Another prior proposed system involved the use of a noncontacting capacitor wherein the patient's foot is placed between the plates of the capacitor. The Achilles tendon is tapped with a percussion hammer and the reflex action is sensed by a change in capacitance of the capacitor. This change is applied to a detector system and a read-out is provided for the operator.

Finally, a system was introduced which utilized a photoelectric device, commonly referred to as the photomotograph, used in conjunction with a standard direct-writing electrocardiograph to permit a simple recording of foot movement. A tap on the Achilles tendon with a percussion hammer causes the patient's foot to move in the light beam, generating a change in photocell voltage which is then recorded on the electrocardiograph paper to give a time position plot of reflex action.

While these prior art systems have proved satisfactory, it has been found desirable to improve the systems for measuring the tendon reflex. With the system of the present invention, a simple office procedure is performed with ease and with a minimum expenditure of time by the physician. The procedure can be performed by the physician's assistant in a matter of a few moments and the results evaluated while the patient is still in the office. Thus, it is ideally suited for an out-patient type of operation in a physician's office. Further, it can be used as a test for screening thyroid patients and following their progress under medication.

Further, the test, as performed by the system of the present invention, could become a valuable part of the complete physical examination record which may be utilized for future comparison as is now commonly recommended for electrocardiograms. With this test, the physician can easily follow the patient's response to therapy, regardless of the type of therapy utilized.

Further, it has been suggested, for example, that one in every twenty persons in the United States have a malfunctioning thyroid glad and this condition causes the patient to carry a higher risk of heart attack, some cancers, and a sluggish functioning of the brain. For this reason, it has been suggested to institute mass screening tests to detect this condition in order that these people may receive the proper medical attention. The simplicity in performing the Achilles reflex test and its accuracy in screening hypothyroid patients particularly lends itself to such mass testing procedures.

With the system of the present invention, an input transducer is interconnected with the patient to provide an output signal indicative of the displacement of the foot in response to the tapping of the Achilles tendon with a percussion hammer. This transducer may take various forms, and for example, the photoelectric technique described above wherein a lamp and a condensing lens in one side of a U-shaped housing directs a beam of light on a photovoltaic cell on the other side of the U-shaped housing. The patient is then positioned in a kneeling configuration on a chair or specially designed kneeling bench. The unit is positioned so that the light beam is partially intercepted by the metatarsal region of the foot. Upon tapping the Achilles tendon with the percussion hammer, the patient's foot is caused to move in the light beam to generate the change in voltage from the photoelectric cell described above.

The output from the transducer is set to an input amplifier which amplifies the signal from the transducer. The output of the input amplifier is fed in one instance to a peak detector and holder circuit which is utilized to detect and hold the highest peak sensed before the peak holder is reset. The output of the peak holder is fed through a one-half voltage divider and then to the input circuit of a comparator circuit. The output of the input amplifier is also fed directly to the input of the comparator circuit wherein the two signals are compared to detect a cross-over when the output of the one-half peak voltage divider exceeds the output from the input amplifier. When this condition occurs, an output signal is generated by the comparator circuit.

This output signal from the comparator circuit is fed to a flip flop which is triggered to the opposite state with every positive going pulse edge from the comparator circuit. As will be seen from a further description of the drawings, positive going edges occur when the reflex wave form reaches one-half of its amplitude in the initial peak and subsequently reaches one-half of its amplitude in a subsequent peak. The output of the flip flop is fed to an integrator circuit which provides a time reading of the duration of the period during which the flip flop was triggered to its opposite state. This output is then fed to a meter or to some other type of output indicating device.

The system further includes an input offset compensator which is a circuit connected to the input amplifier for providing a compensating voltage for the input amplifier to force the input amplifier to provide a zero output signal when there is zero input from the transducer. The system further includes a reset switch which is connected to the input offset compensator circuit, the peak holder circuit, the flip flop circuit, and the integrator circuit to reset and initialize these circuits prior to taking a measurement.

OBJECTS AND BRIEF DESCRIPTION OF THE DRAWINGS

Accordingly, it is one object of the present invention to provide a new and improved diagnostic instrument for medical use.

It is another object of the present invention to provide an improved diagnostic instrument for use in recording body response when outside stimulus is applied.

It is another object of the present invention to provide an improved instrument for use in diagnosing body malfunction.

It is still a further object of the present invention to provide an improved diagnostic instrument for timing the Achilles reflex in response to a tap on the Achilles tendon by a percussion hammer.

It is still another object of the present invention to provide an improved diagnostic instrument for measuring the Achilles reflex time of a patient as an aid in diagnosing malfunctioning of the thyroid.

It is still a further object of the present invention to provide an improved diagnostic instrument for use in connection with treating thyroid patients which includes an improved peak detector and amplitude cross-over detector circuit.

It is still a further object of the present invention to provide an improved diagnostic instrument for use in detecting thyroid malfunction which includes an improved input stage having an off-set compensator circuit.

It is still a further object of the present invention to provide an improved diagnostic system for use in conjunction with detecting thyroid malfunction in a patient which includes an improved reset system for the various subcircuits of the system.

It is still another object of the present invention to provide an improved diagnostic system for use in conjunction with treating thyroid patients which is inexpensive to manufacture, reliable in use, and simple to operate.

Other objects, features, and advantages of the present invention will become apparent from the subsequent description and the appended claims, taken in conjunction with the accompanying drawings, in which:

FIG. 1 is a time-position plot of the reflex action of a patient's foot in response to a tap on the Achilles tendon with a percussion hammer;

FIG. 2 is a block diagram of the preferred embodiment of the system of the present invention;

FIG. 3 is a timing chart illustrating the various voltage levels of certain portions of the block diagram of FIG. 1; and FIG. 4 is a schematic diagram illustrating the specific details of the block diagram of FIG. 2.

DETAILED DESCRIPTION OF THE DRAWINGS

Referring now to FIG. 1, there is illustrated a time-position plot of the Achilles tendon reflex upon being struck by a reflex hammer. Particularly, the hammer tap occurs where indicated and the reaction of the Achilles tendon causes a foot reflex which initially peaks at a point 10, the amplitude then dropping to a negative value at a point 12. The muscle reacts to produce a peak contraction at 14, the trace then falling off to a half-relaxation point 16. It is this half-relaxation point which will become critical as will be seen from a further description. The trace then falls off to a level indicated at 18 until such time as a second hammer tap occurs. It is this trace which the system of the present invention is adapted to sense and to time certain intervals between certain portions of the trace. It should be noted that a hammer tap artefact occurs to produce a half-relaxation point, which point would occur at point 20.

Referring now to FIG. 2, there is illustrated a block diagram of a preferred embodiment of the system of the present invention. Particularly, the patient's foot is positioned in a transducer which may take a variety of configurations, as for example, the magnetic or optical systems described above. Upon striking the Achilles tendon of a patient with a reflex hammer, an input wave form 22 will be produced, which input wave form will be fed to an input conductor 24.

The input conductor 24 is connected to the input circuit of an input amplifier circuit 26, the output of the input amplifier circuit generating a wave form 30 which is identical to the wave form 22 with the exception that it is somewhat amplified. The wave form A is illustrated in FIG. 3 at 30. The output of the input amplifier 26 is fed to the input circuit of a comparator circuit 32 by means of a conductor 34 and to the input circuit of a peak holder circuit 36 by means of a conductor 38.

The output of the peak holder circuit is fed through a voltage divider circuit 40 which includes a pair of resistors 42, 44, the center point of the resistors 42, 44 being tapped and connected to the input circuit of the comparator circuit by means of a conductor 46. Thus, the output of the peak holder rises to a sensed peak and is held there until a larger peak is sensed, in which case the output of the peak holder rises to the new peak. These amplitudes are then divided by means of the resistors 42, 44 and fed to the tap conductor 46.

Referring to FIG. 3, it is seen that the wave form B from FIG. 2 and given reference numeral 50, as fed to the input circuit of the comparator circuit 32, rises to a level which corresponds to the sensing of the peak 52. The wave form 30 then drops to some lower level below the wave form 50 and then rises to a second peak 54. The signal level on wave form 50 does not rise until such time as the magnitude of the wave 30 rises above the peak 52 which occurs sometime after the second cross-over of the wave form 50 and 30. The wave form 50 will then follow the wave 30 to the new peak 54 and will maintain a level after the new peak 54. The wave form 30 then drops off and crosses the wave form 50. The cross-over at point 56 and at point 58 are critical to the circuit being described in conjunction with description of FIG. 2.

The comparator circuit 32 compares the input wave form A and the input wave form B, particularly waves 30 and 50, the comparator circuit detecting when the wave forms 30 and 50 cross with the wave form 30 going below the wave form 50. As noted in conjunction with the description of FIG. 3, this occurs at two points, particularly points 56 and 58. At each of these points 56 and 58, the comparator circuit 32 will switch states, the signal level following a curve C as indicated by wave form 60 in FIG. 3.

Thus, referring to FIG. 3, when the wave form 30 crosses-over the wave form 50 at point 56, the output of comparator 32 will switch from a zero level to a positive level 62 by a sharp positive going edge. When the wave form 30 again crosses the wave form 50 but going in the positive direction, the wave form 60 drops to the zero level again with a sharp negative going edge. Upon the crossing of the wave form 30 at point 58, a second positive going edge is created when the wave form 60 rises to the positive level at 64. Thus, two positive going edges are created at cross-overs 56 and 58.

The wave form 60 is fed to the input of a flip flop circuit 66, the flip flop circuit, as will be seen from a description of FIG. 4, being responsive to positive going edges due to the fact that a steering network has been provided at the input circuit to the flip flop 66. Accordingly, at the cross-over 56, the flip flop 66 switches from a set state to reset state as indicated by wave form 70. The output of flip flop 66, as fed to conductor 72, goes from a zero level at 74, indicated on wave form D in FIG. 3, to a negative level in response to the generation of the positive edge at cross-over 56 (wave forms A and B in FIG. 3). Upon the occurrence second cross-over at 58, the flip flop again rises from a negative level to a positive level at 76 in response to the second zero going edge in wave form 60.

The output of the flip flop 66 is fed to the input circuit of an integrator circuit 80, the output of the integrator circuit going from a zero level to some positive voltage at 82 on FIG. 3 (wave form E), the level of wave form E at 82 being determined by the amount of time lapse between cross-over 56 and cross-over 58. Accordingly, if cross-over 58 occurred a shorter period of time after cross-over 56, the voltage level 82 would be somewhat less due to the lesser duration of time permitted for the integrator circuit to operate. Correlatively, if the cross-over point 58 occurred later than indicated, the voltage level 82 would be somewhat higher.

The output of integrator circuit 80 is fed to a meter output 84 which indicates the voltage level at 82 and thus provides a direct reading of the time lapse between cross-over 56 and cross-over 58. Thus, the circuit provides a direct read-out of the Achilles reflex time between half-relaxation points of the wave form A. A majority of authorities have found that the half-relaxation points are extremely reliable in providing an indication of the Achilles reflex time. Other authorities have relied on the time between the peaks 10 and 14, which may be measured by the system of the present invention with slight modification.

The circuit of FIG. 2 also includes an input offset compensator circuit 90, which circuit 90 provides an input signal to the input amplifier by means of a conductor 92, which signal will supply the input amplifier circuit 26 with sufficient current to offset any generation of an output current when there is zero input from the transducer as fed to input conductor 24. Thus, the circuit 90 merely varies the voltage level on conductor 92 either positive or negative, depending on the voltage required to preset the signal on conductors 34 and 38 to zero when there is no input being fed to input conductor 24.

The system also includes a reset switch circuit 94, which reset switch circuit is connected to the input offset compensator circuit by means of a conductor 96, to the peak holder circuit by means of a conductor 98, to the flip flop circuit 66 by means of a conductor 100 and to the integrator circuit by means of a conductor 102.

As will be seen from a description of FIG. 4, the reset switch is connected to the input off-set compensator to provide a connection between the input off-set compensator circuit and the input amplifier at the initial start of the measuring cycle. This will provide a circuit for holding input voltage at a set point to provide zero output from the input amplifier circuit 26. The reset switch is connected to the peak holder circuit to ground a capacitor within the peak holder circuit upon initializing the system. The flip flop is connected to the reset switch to ensure that the flip flop is set to a particular state when the system is initialized. Finally, the reset switch circuit 94 is connected to the integrator circuit 80 to ensure that an integrating capacitor connected in the integrator circuit 80 is fully discharged upon initializing the system.

Referring now to FIG. 4, there is illustrated the specific circuit details which correspond to the block diagram of FIG. 2. While the circuit components to be described form the preferred embodiment, it is to be understood that other circuit components could be utilized to perform the same function such as, for example, discrete components or printed circuit boards.

Specifically, the input signal from the transducer associated with the patient's foot is fed to the input conductor 24, which conductor 24 is connected to the input circuit of an operational amplifier 110 forming the input amplifier. The input amplifier 110 is connected in the typical manner wherein a positive source of 15 volt potential is connected to a terminal 112 and a negative source of potential is connected to the input terminal 114. The output of the operational amplifier is connected to a node 116 which provides an output signal which is identical to the input signal with the exception that the signal is amplified. The amplifier 110 also includes a second input through a resistor 118 for a purpose to be explained hereinafter.

The output from the input amplifier 110 is fed to a peak detector and holder circuit 120 by means of a diode 122 and a conductor 124. The peak detection portion of the circuit includes a capacitor 126, which capacitor is grounded at one end thereof and the other end of the capacitor is connected to the conductor 124. The capacitor 126 will be charged in accordance with the output signal from operational amplifier 110 to a point where the signal peaks-out. Thereafter, the charge on capacitor 126 will remain the ame until such time as the signal from operational amplifier 110 increases above the previous peak. At this time, the charge on capacitor 126 will again increase to detect any further increased peaks being fed thereto from the operational amplifier 110 prior to resetting the detector circuit.

The peak detector and holder circuit 120 further includes an operational amplifier 130 which includes a feed back circuit from the output thereof to the upper input by means of a conductor 132. The amplifier 130 is connected as a unity-gain amplifier and the conductor 132 ensures that the output from the amplifier 130 exactly follows the charge on capacitor 126.

The output of input amplifier 110 is also fed forward to an operational amplifier 134, which operational amplifier 134 is connected as a comparator circuit. The signal from operational amplifier 110 is fed thereto by means of a conductor 136, the other input of the operational amplifier 134 being connected to the peak detector and holder circuit 120 by means of a voltage divider circuit 138 and a conductor 140.

The voltage divider circuit 138 includes a first and second resistor 142, 144 the values of which are selected such that the voltage being fed to conductor 140 is one-half the magnitude of signal being fed to the voltage divider circuit 138 from the operational amplifier 130. In this way, the signal on conductor 140 will follow the wave form 50 described in conjunction with FIG. 3 and the wave form on conductor 136 will follow the wave form 30 also described in conjunction with FIG. 3. The voltage divider circuit 138 also includes a source of negative 15 volt potential connected to an input terminal 148, this potential being fed to the voltage divider circuit by means of a resistor 150. This latter circuit is provided to provide a negative off-set for the curve 150 to preclude any false readings from the comparator circuit 134 before the cross-over points 56 and 58 described in conjunction with FIG. 3.

The output of the comparator circuit 134 follows the curve 60 described in conjunction with the description of FIG. 3, this signal being fed to an output conductor 152, this latter conductor being connected to a flip flop circuit 154 through a bias circuit 156 and a diode steering network 158. The bias circuit includes a pair of resistors 160, 162, the upper end of resistor 160 being connected to a negative 15 volt potential and the lower end of resistor 162 being grounded. The diode steering network includes a pair of diodes 164, 166, these diodes being utilized to render the flip flop circuit 154 responsive to positive going edges as described in conjunction with curve 60 of FIG. 3.

The flip flops circuit 154 is a conventional flip flop and includes a pair of npn transistors 170, 172, which transistors are cross-coupled by means of circuit 174. The output of transistor 172 is cross-coupled to the base electrode of transistor 170 by means of a transistor 176, the transistor 176 being connected in an emitter-follower configuration, the emitter electrode of transistor 176 being coupled through a resistor-capacitor network 177 similar to the cross-coupling network 174. In this way the output of the flip flop 154 follows the curve 170 and produces a sharp switching from one state to the other. The output of the flip flop circuit 154 is connected to the collector-electrode of transistor 172 by means of a conductor 178 this output signal being fed to the input circuit of an operational amplifier 180, which operational amplifier 180 is connected in an integrator circuit. The connection between the output of flip flop 154 and the input of integrator 180 is accomplished by means of a resistor 182 and a diode 184, the diode 184 ensuring that the proper polarity signal is fed to the operational amplifier 180.

The operational amplifier 180 includes an integrating capacitor 186, which integrating capacitor is connected between the output of the operational amplifier 180 and the input thereof connected to diode 184. The other input of operational amplifier 180 is grounded through a resistor 188.

The output of the integrator circuit 180 is connected such that the output will follow curve 82 as described in conjunction with FIG. 3. Thus, as long as the flip flop circuit is in the reset state, the capacitor 186 will charge to raise the level of the output of the operational amplifier 180. This current output is fed to a meter 190 by means of a resistor 194. The opposite end of the meter 190 is grounded at 196.

Referring now to the upper part of FIG. 4, there is illustrated an input off-set compensator circuit 200 which includes an operational amplifier 202. The operational amplifier 202 includes a feed back circuit in the form of a resistor 206. As will be seen from a further description of the reset circuit, the capacitor 204 is initially charged with a voltage which is representative of the output of the input amplifier 110. This charge will cause operational amplifier 202 to provide an output signal on a conductor 208 which is commensurate with the charge on capacitor 204. This conductor 208 is connected to the upper input circuit of the input amplifier 110 through the conductor 208 and a resistor 210 and the resistor 118. In this way the operational amplifier will provide a signal to ensure that the output of operational amplifier 110 is zero with a zero input signal impressed on conductor 24.

Referring now to a reset circuit 216, it is seen that the reset circuit includes a ganged switch 220 which has a plurality of blades 222, 224, 226, and 228. The switch 220 is operated by means of a button (as illustrated) or a lever switch and the switch is mechanically devised such that all of the blades 222 – 228 contact the respective contact point simultaneously and break their respective contact points in a particular sequence. In accordance with the way that the circuit is devised, the contact points break in the order of contacts 222, 224, 226, and 228.

Referring specifically to the circuit details of the switch, it is seen that the blade 222 connects conductors 230, 232 together, the conductor 230 being connected to the output of operational amplifier 110 through a resistor 234. The conductor 232 is connected to the upper end of capacitor 204. Thus, when the switch blade 222 contacts its respective contact points, the output of operational amplifier 110 is connected to the capacitor 204 to charge the capacitor in accordance with the output of operational amplifier 110. This occurs when there is no input being fed to the input conductor 24.

The second contact blade 224 connects the capacitor 126, connected to the input of operational amplifier 130, to ground through a conductor 240, a conductor 242, and the switch blade 222 and the conductor 232 to ground through the capacitor 204, so that the capacitor is approximately ground when the switch is closed, there being a slight charge on the capacitor 204 due to the output current flowing from the operational amplifier 110. However, capacitor 126 need only be approximately grounded due to the fact that the signal level being impressed on capacitor 126 far exceeds the signal level on capacitor 204.

The switch blade 226 is utilized to connect a pair of conductors 248, 250 together, the conductors 248, 250 being connected across the capacitor 186 connected in the integrator circuit associated with operational amplifier 180. When the contact blade 226 engages the respective contact points, the capacitor 186 is short-circuited to discharge that capacitor.

The blade 228 is utilized to reset the flip flop circuit 154 to a initial state by grounding the base electrode of transistor 176. This is accomplished by connecting conductors 254, 256, and the conductor 178 to ground at 258 through the switch blade 228. Thus, when the blade 228 contacts its respective contact points, the flip flop 154 is switched to the set state.

Accordingly, when the switch button is released, the charge on blade 222 will initially disengage first to remove the source of potential from the capacitor 204. Thus, capacitor 204 will initially be set with a voltage which corresponds to the output signal from the operational amplifier 110 with a zero input impressed on conductor 224. The blade 224 will release second to release the discharge path from capacitor 126. The switch blade 226 will release third which discharges the capacitor 186 after the setting of the C voltage on capacitor 204 and the discharging of capacitor 126. Finally, the set state of flip flop 154 is assured by releasing the blade 228 after the releasing of the other blades and the gang switch 220.

While it will be apparent that the preferred embodiment of the invention disclosed is well calculated to fulfill the objects above stated, it will be appreciated that the invention is susceptible to modification, variation and change without departing from the proper scope or fair meaning of the subjoined claims.

What is claimed is:

1. A system for sensing the lapse of time between the peak contraction and the one-half relaxation point on a curve created by sensing the displacement of a foot in response to tapping the achilles tendon of the foot, the resulting curve having at least a first and second peak component having first and second peaks, the system comprising transducer means positioned to respond to the displacement of the foot and generating the curve, means connected to said transducer means for detecting a characteristic of the first peak of the curve and generating a first signal in response thereto and detecting the same characteristic of the second peak and generating a second signal in response thereto, said characteristic being relaxation points defined by a ratio of the characteristic point amplitude to the peak amplitude of said first and second peak components, bi-stable circuit means connected to said detector means having a first and second stable state, said bi-stable circuit means being in said first state in response to said first signal and being switched to said second state in response to said second signal, integrator circuit means including output means connected to said bi-stable circuit means and responsive to said first and second stable states, said integrator circuit means timing the period between said first and second characteristic and providing an output thereof, and reset circuit means connected to said detector means, bi-stable circuit means and said integrator circuit means for resetting said various means subsequent to the occurrence of said second characteristic.

2. The improvement of claim 1 wherein said characteristics are a one-half relaxation point of said peak components.

3. The improvement of claim 1 wherein said detector means includes a peak holder circuit connected to said transducer means and a feed-forward circuit connected in parallel with said peak holder circuit to feed said curve forward of said peak holder circuit.

4. The improvement of claim 3 wherein said detector means includes comparator circuit means connected between said peak holder circuit and said parallel circuit and said bi-stable circuit means, said peak holder circuit means and said parallel circuit forming two inputs to said comparator circuit for comparison of signals from said feed-forward and said peak holder circuits.

5. The improvement of claim 4 wherein said detecting means further includes an input amplifier connected in circuit before said peak holder circuit and said parallel circuit to receive said first and second peaks.

6. The improvement of claim 5 wherein said peak holder circuit includes a voltage divider to establish said ratio of the characteristic amplitude point on said first and second peak components.

7. The improvement of claim 6 wherein said comparator circuit means compares said ratio amplitude and said first and second curve amplitude peaks, said comparator circuit means generating an output signal in response to a relationship between said first peak amplitude and said ratio amplitude of said first peak component and another output signal in response to a relationship established between said second peak amplitude and said ratio amplitude of said second peak component.

8. The improvement of claim 7 wherein said output signal sets said bi-stable circuit means in said first state and said another output signal sets said bi-stable circuit means in said second state.

9. The improvement of claim 8 wherein said integrator circuit means includes an operational amplifier connected as an integrator and an output meter, said output meter indicating the voltage level at the output of said operational amplifier.

10. The improvement of claim 9 wherein said reset circuit means includes a multi-poled switch connected to said bi-stable circuit means, said integrator circuit means and said peak holder circuit, a first set of said poles, when closed, setting said bi-stable circuit means to said first state, a second set of said poles setting said integrator circuit means to substantially zero and a third set of said poles setting said peak holder circuit to zero.

11. The improvement of claim 10 wherein said system further includes an input off-set compensator circuit connected to said input amplifier said input off-set compensator circuit being selectively adjustable to provide a signal to said input amplifier to set the output of said input amplifier to zero when said curve is at a zero signal level.

12. The improvement of claim 11 wherein said reset switch includes a fourth set of poles connected to said compensator circuit, said fourth set of poles, when closed, connecting said input off-set compensator circuit to said input amplifier.

13. The improvement of claim 12 wherein said system includes means for actuating said poles in the order of said fourth set, said third set, said second set, and said first set.

14. The improvement of claim 1 wherein said detector means includes a peak holder circuit and a feed-forward circuit connected in parallel with said peak holder circuit to feed said curve forward of said peak holder circuit.

15. The improvement of claim 14 wherein said detector means includes comparator circuit means connected between said peak holder circuit and said parallel circuit and said bi-stable circuit means, said peak holder circuit and said parallel circuit forming two inputs to said comparator circuit means for comparison thereby.

16. The improvement of claim 15 wherein said detecting means further includes an input amplifier connected in circuit before said peak holder and said parallel circuits to receive said first and second peaks.

17. The improvement of claim 16 wherein said peak holder circuit includes a voltage divider to establish a preselected point on said first and second peak components.

18. The improvement of claim 17 wherein said comparator circuit means compares said relaxation points and said first and second curve peaks, said comparator circuit means generating an output signal in response to a relationship between said first peak and said relaxation point on said first peak component and another output signal in response to a relationship established between said second peak and said relaxation point of said second peak component.

19. The improvement of claim 18 wherein said output signal sets said bi-stable circuit means in said first state and said another output signal sets said bi-stable circuit means in said second state.

20. The improvement of claim 19 wherein said integrator means includes an operational amplifier connected as an integrator and an output meter, said output meter indicating the voltage level at the output of said operational amplifier.

21. The improvement of claim 20 wherein said reset circuit means includes a multi-poled switch connected to said bi-stable circuit means, said integrator circuit means and said peak holder circuit, a first set of said poles, when closed, setting said bi-stable circuit means to said first state, a second set of said poles setting said integrator circuit means to substantially zero and a third set of said poles setting said peak holder circuit to zero.

22. The improvement of claim 21 wherein said system further includes an input off-set compensator circuit connected to said input amplifier, said input off-set compensator circuit being selectively adjustable to provide a signal to said input amplifier to set the output of said input amplifier to zero when said curve is at a zero signal level.

23. The improvement of claim 22 wherein said reset switch includes a fourth set of poles connected to said input off-set compensator circuit, said fourth set of poles, when closed, connecting said input off-set compensator circuit to said input amplifier.

24. The improvement of claim 23 wherein said system includes means for actuating said poles in the order of said fourth set, said third set, said second set, and said first set.

* * * * *

UNITED STATES PATENT AND TRADEMARK OFFICE
CERTIFICATE OF CORRECTION

PATENT NO. : 3,938,503

DATED : February 17, 1976

INVENTOR(S) : Vis, Vincent A.

It is certified that error appears in the above—identified patent and that said Letters Patent are hereby corrected as shown below:

Column 1, line 33, "in" should read --is--;
Column 2, line 10, "glad" should read --gland--;
Column 5, line 34, "Accrodingly" should read -- Accordingly --.
Column 6, line 50, "ame" should read -- same--.

Signed and Sealed this twenty-fifth Day of May 1976

[SEAL]

Attest:

RUTH C. MASON
*Attesting Officer*

C. MARSHALL DANN
*Commissioner of Patents and Trademarks*